United States Patent
Nakamura et al.

(10) Patent No.: US 7,022,738 B2
(45) Date of Patent: Apr. 4, 2006

(54) α-KETOAMIDE DERIVATIVE AND USE THEREOF

(75) Inventors: Masayuki Nakamura, Kobe (JP); Jun Inoue, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/521,764

(22) PCT Filed: Jul. 11, 2003

(86) PCT No.: PCT/JP03/08878

§ 371 (c)(1), (2), (4) Date: Mar. 31, 2005

(87) PCT Pub. No.: WO2004/009537

PCT Pub. Date: Jan. 29, 2004

(65) Prior Publication Data

US 2005/0165113 A1    Jul. 28, 2005

(30) Foreign Application Priority Data

Jul. 22, 2002   (JP) .............................. 2002-212288

(51) Int. Cl.
*A61K 31/18* (2006.01)
*A61K 38/05* (2006.01)
*C07C 311/18* (2006.01)
(52) U.S. Cl. ........................... 514/604; 514/19; 564/94
(58) Field of Classification Search .................. 514/19, 514/604; 564/94
See application file for complete search history.

(56) References Cited

U.S. PATENT DOCUMENTS 6,057,290 A    5/2000   Fukiage et al. ................ 514/12

6,423,691 B1 *  7/2002   Azuma et al. ................ 514/19

FOREIGN PATENT DOCUMENTS

| EP | 0 641 563 | 3/1995 |
|---|---|---|
| JP | 6-29229 | 4/1994 |
| WO | 96/16079 | 5/1996 |

OTHER PUBLICATIONS

Crawford et al., "The Design of peptidyldiazomethane inhibitors to distinguish between the cysteine proteinases calpain II, cathepsin L and cathepsin B", Biochem. J., vol. 253, pp. 751-758, (1988).

Angliker et al., "Inactivation of Calpain by Peptyidyl Fluoromethyl Ketones", J. Med. Chem., vol. 35, No. 2, pp. 216-220, (1992).

Azuma et al., "Cysteine protease inhibitor E64 reduces the rate of formation of selenite cataract in the whole animal", Current Eye Research, vol. 10, No. 7, pp. 657-666, (1991).

Wang et al., "Calpain inhibition: an overview of its therapeutic potential", Trends in Pharmaceutical Sciences (TIPS), vol. 15, pp. 412-419, (1994).

* cited by examiner

*Primary Examiner*—Peter O'Sullivan
(74) *Attorney, Agent, or Firm*—Wenderoth, Lind & Ponack, L.L.P.

(57) ABSTRACT

The present invention provides a compound represented by the formula (I):

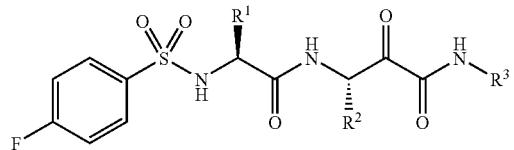

wherein $R^1$, $R^2$ and $R^3$ each represents a lower alkyl group.

6 Claims, No Drawings

α-KETOAMIDE DERIVATIVE AND USE THEREOF

This application is a U.S. national stage of International Application No. PCT/JP03/008878 filed Jul 11, 2003.

1. Technical Field

The present invention relates to a novel α-ketoamide derivative having calpain inhibitory activity. Also, the present invention relates to a medicament comprising the novel α-ketoamide derivative.

2. Background Art

Calpain is one of the intracellular proteases ubiquitously present in a living body, which is activated by $Ca^{2+}$. It has been elucidated to this day that abnormal activation of calpain is involved in various diseases such as cerebral apoplexy, subarachnoid hemorrhage, Alzheimer's disease, ischemic disease, muscular dystrophy, cataract, platelet aggregation disorder, arthritis or the like (Trends in Pharmacological Sciences, vol. 15, page 412, 1994).

On the other hand, it has been reported that a calpain inhibitor is effective for maintaining permeability of lens in an experimental cataract model of cultured lens (Current Eye Research, vol. 10, Pages 657 to 666, 1991) and is useful as a therapeutic agent for cataract, etc. (WO 93/23032).

Examples of calpain inhibitors which have been so far reported include peptidyl halomethane derivatives (JP-B-29229/1994), peptidyl diazomethane derivatives (The Biochemical Journal, vol. 253, pages 751 to 758, 1988, Journal of Medicinal Chemistry, vol. 35, pages 216 to 220, 1992), peptidyl aldehyde derivatives (EP-A-0771565, U.S. Pat. No. 6,057,290, etc.) and the like, however, none of the above inhibitors has been put to practical use.

DISCLOSURE OF THE INVENTION

The present inventors have conducted intensive studies to provide a compound having calpain inhibitory activity and, as a result, created an α-ketoamide derivative having potent calpain inhibitory activity. They have conducted further studies and finally completed the present invention.

Namely, the present invention relates to (1) A compound represented by the formula (I)

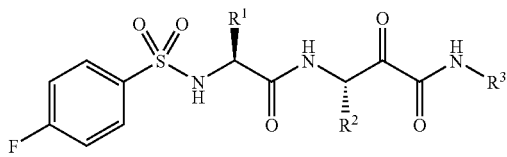

(I)

wherein $R^1$, $R^2$ and $R^3$ each represents a lower alkyl group;

(2) the compound according to the above (1), wherein $R^1$, $R^2$ and $R^3$ each represents an alkyl group having 3 or 4 carbon atoms;

(3) (3S)-N-butyl-3-((2S)-2-(((4-fluorophenyl)sulfonyl)amino)-3-methylbutanoylamino)-5-methyl-2-oxohexanamide;

(4) a medicament comprising a compound represented by the formula (I)

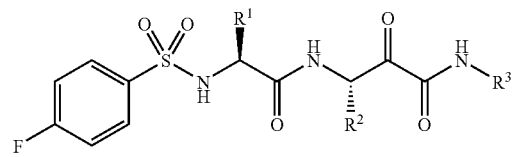

(I)

wherein $R^1$, $R^2$ and $R^3$ each represents a lower alkyl group;

(5) the medicament according to the above (4), which is a calpain inhibitor;

(6) the medicament according to the above (4), which is a prophylactic or therapeutic agent for a disease related to calpain;

(7) a pharmaceutical composition comprising a compound represented by the formula (I)

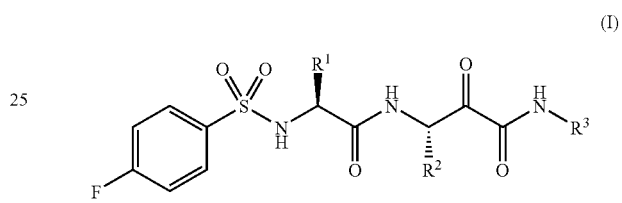

(I)

wherein $R^1$, $R^2$ and $R^3$ each represents a lower alkyl group, and a pharmaceutically acceptable carrier;

(8) the pharmaceutical composition according to the above (7), which is a calpain inhibitor;

(9) a method for the treatment of a disease related to calpain, which comprises administering an effective amount of a compound represented by the formula (I)

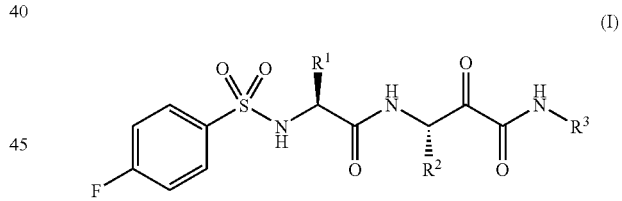

(I)

wherein $R^1$, $R^2$ and $R^3$ each represents a lower alkyl group, to a mammal in need of treatment; and

(10) use of a compound represented by the formula (I)

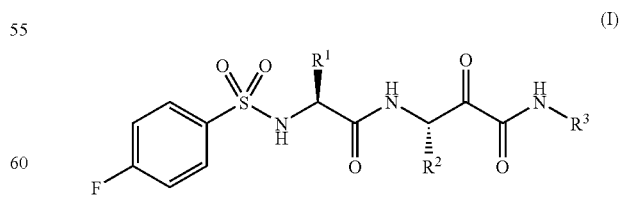

(I)

wherein $R^1$, $R^2$ and $R^3$ each represents a lower alkyl group as a calpain inhibitor.

In the above formula (I), preferable examples of the lower alkyl group represented by $R^1$, $R^2$ or $R^3$ include a straight or branched alkyl group having 1 to 6 carbon atoms, specifically, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl, etc., and more preferably a straight or branched alkyl group having 3 or 4 carbon atoms. Particularly preferable examples of the lower alkyl for $R^1$, $R^2$ and $R^3$ are isopropyl, isobutyl and butyl, respectively.

In addition, the present invention includes a variety of solvates, polymorphs and pro-drugs of the compound (I) of the present invention as well as the compound (I).

The compounds of the present invention can be prepared, for example, according to the following reaction scheme:

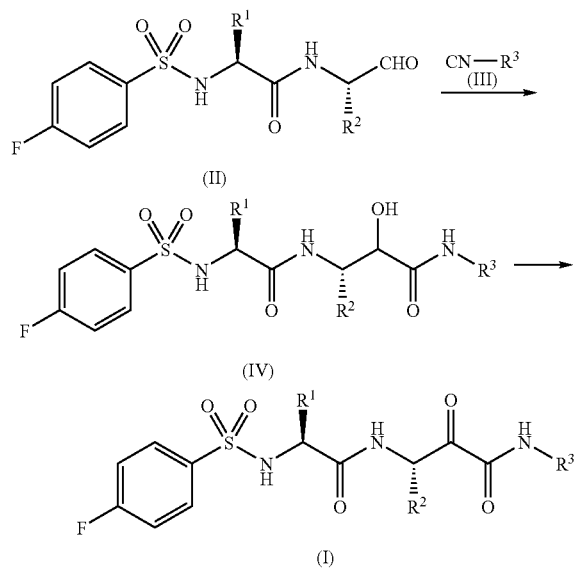

in which each symbol has the same meaning as defined above.

A compound represented by the formula (IV) (hereinafter, it may be referred to as compound (IV)) can be prepared by dissolving a peptidyl aldehyde compound represented by the formula (II) (hereinafter, it may be referred to as compound (II)) which is synthesized according to the method described in, for example, EP-A-0771565 or U.S. Pat. No. 6,057,290 and an isocyanide reagent represented by the formula (III) (hereinafter, it may be referred to as compound (III)) in a commonly used organic solvent, and subjecting the resulting solution to Passerini reaction in the presence of trifluoroacetic acid and pyridine (Org. Lett., vol. 2, pages 2769 to 2772, 2000). Examples of the commonly used organic solvent include conventional solvents not adversely affecting the reaction or a mixture thereof, such as dichloromethane, N,N-dimethylformamide, dimethylsulfoxide, tetrahydrofuran, methanol, ethanol, benzene, toluene, ethyl acetate, etc., and among which dichloromethane is preferable. The amount of the isocyanide reagent used is about 1- to 10-fold mole equivalents, preferably about 1- to 2-fold mole equivalents of the compound (II). The amount of the trifluoroacetic acid used is about 1- to 20-fold mole equivalents, preferably about 1- to 3-fold mole equivalents of the compound (II). The amount of the pyridine used is about 1- to 20-fold mole equivalents, preferably about 3- to 5-fold mole equivalents of the compound (II). The reaction temperature is not particularly limited so long as it falls within the range where no undesirable side reaction occurs, and usually the reaction is carried out under cooling, at room temperature or under mild heating, preferably at a temperature within the range of ice-cooling to room temperature.

The compound (I) can be obtained by subjecting the compound (IV) to an oxidation reaction. The oxidation reaction is carried out by per se conventional methods, including those classified into (i) chromium oxidation such as pyridinium dichromate (PDC) oxidation, pyridinium chlorochromate (PCC) oxidation, Jones oxidation and Collins oxidation, and (ii) DMSO oxidation such as Swern oxidation, DMSO/sulfur trioxide-pyridine complex oxidation, DMSO/dicyclohexcylcarbodiimide (DCC) oxidation, DMSO/oxalyl chloride oxidation, Dess-Martin oxidation using Dess-Martin periodinane, hypohalous acid oxidation and N-halogenocarboxylic amide oxidation, and among which Dess-Martin oxidation is preferable. In carrying out Dess-Martin oxidation, the compound (IV) is dissolved in a commonly used organic solvent and Dess-Martin reagent is added thereto. Examples of the commonly used organic solvents include conventional solvents not adversely affecting the reaction or a mixture thereof, such as dichloromethane, N,N-dimethylformamide, dimethyl sulfoxide, tetrahydrofuran, methanol, ethanol, benzene, toluene, ethyl acetate, etc., and among which dichloromethane is preferable. The amount of the Dess-Martin reagent is about 1- to 20-fold mole equivalents, preferably 1- to 3-fold mole equivalents of the compound (IV). The reaction temperature is not particularly limited so long as it falls within the range where no undesirable side reaction occurs, and usually the reaction is carried out under cooling, at room temperature or under mild heating, preferably at a temperature within the range of ice-cooling to room temperature. The ketoamide derivatives thus obtained can be separated and purified by conventional separation and purification methods including, for example, concentration, concentration in vacuo, solvent extraction, crystallization, recrystallization, solvent transfer, chromatography or the like.

Specific examples of compounds (I) prepared according to the above method include (3S)-N-butyl-3-((2S)-2-(((4-fluorophenyl)sulfonyl)amino)-3-methylbutanoylamino)-5-methyl-2-oxohexanamide, etc.

The compounds of the present invention have not yet been reported in literatures, and thus they are novel. As shown in Test Examples which will be hereinafter described, the compounds of the present invention have an excellent calpain inhibitory activity. Accordingly, a medicament containing a compound of the present invention as active ingredient, optionally in combination with a carrier, etc. which will be hereinafter described, is useful as a calpain inhibitor.

The medicament containing a compound of the present invention is useful as a prophylactic or therapeutic agent for mammalian (e.g. human, rat, mouse, rabbit, cattle, pig, dog, cat) diseases related to calpain such as ischemic disease, immunologic disease, Alzheimer's disease, osteoporosis, diseases caused by brain tissue damage, cataract, glaucoma, retinochoroidal disease, posterior eyeball complications due to photocoagulation (e.g. macular edema, retinal detachment, optic neuritis, visual field defect, light sense defect, dyschromatopsia, etc.), a disease involving neovascularization or the like. In addition, a compound of the present invention has excellent tissue transport and high absorbability as well as high safety with very low toxicity.

The medicament containing a compound of the present invention can be administered systemically or locally. Besides oral administration, the systemic administration includes parenteral administration route such as intravenous injection, subcutaneous injection, intramuscular injection and the like. In case of the local administration, the medicament is applied via transdermal, mucous membrane, nasal or intraocular route, etc.

The dosage form of the medicament containing a compound of the present invention includes solid preparations (e.g. powders, granules, tablets, capsules, suppositories, etc.) and liquid preparations (e.g. syrups, injections, eye drops, nasal drops, etc.). In the production of granules or tablets, any dosage form can be prepared with the use of, for example, excipients (e.g. lactose, sucrose, glucose, starch, crystalline cellulose, etc.), lubricants (e.g. magnesium stearate, talc, stearic acid, calcium stearate), disintegrators (e.g. starch, carmellose sodium, calcium carbonate, etc.), or binders (e.g. starch paste, hydroxypropylcellulose solution, carmellose solution, gum arabic solution, gelatin solution, sodium alginate solution, etc.). Further, granules and tablets may be coated with a coating agent (e.g. gelatin, white sugar, gum arabic, carnauba wax, etc.) or an enteric coating agent (e.g. cellulose acetate phthalate, methacrylic copolymer, hydroxypropylcellulose phthalate, carboxymethylethyl cellulose, etc.).

In the production of capsules, suitable excipients such as magnesium stearate, calcium stearate, talc and light silicic acid anhydride, etc., for improving flowability and lubricity; crystalline cellulose, lactose, etc. for increasing flowability under pressure, and the above-mentioned disintegrators are appropriately selected and added to the compound of the present invention, mixed or granulated homogenously and filled in capsules, or alternatively, the granulated products may be coated with a suitable coating agent and filled in capsules. They may be encapsulated with an appropriate capsule base (e.g. gelatin) having increased plasticity endowed with addition of glycerin or sorbitol. If required, coloring agents, preservatives (e.g. sulfur dioxide, parabens such as methyl p-oxybenzoate, ethyl p-oxybenzoate and propyl p-oxybenzoate), etc. may be added to the capsule preparations. Enteric coated capsules, gastric resistant capsules or release controlled capsules may be formulated in addition to conventional capsule preparations. In the case of enteric coated capsule preparations, they can be prepared by filling regular capsules with the compound which is coated with an enteric coating agent or the compound to which said appropriate excipient is added. Alternatively, the capsule itself may be coated with an enteric coating agent, or an enteric polymer as a base may be molded into enteric coated capsules.

In the production of suppositories, an appropriate suppository base (e.g. cacao butter, macrogol, etc.) can be selected and used.

In the production of syrups, an appropriate stabilizer (e.g. sodium edetate, etc.), suspending agent (e.g. gum arabic, carmellose, etc.), corrigent (e.g. simple syrup, glucose, etc.), perfume or the like can be selected and used.

In the production of injections, eye-drops or nasal drops, they can be produced by dissolving or dispersing the compound of the present invention in a solution containing a pharmaceutically acceptable additive such as isotonic (e.g. sodium chloride, potassium chloride, glycerin, mannitol, sorbitol, boric acid, borax, glucose, propylene glycol, etc.), buffer (e.g. phosphate buffer, acetate buffer, borate buffer, carbonate buffer, citrate buffer, Tris buffer, glutamate buffer, ε-aminocapronate buffer, etc.), preservative (e.g. methyl p-oxybenzoate, ethyl p-oxybenzoate, propyl p-oxybenzoate, chlorobutanol, benzyl alcohol, benzalkonium chloride, sodium dehydroacetate, sodium edetate, boric acid, borax, etc.), thickener (e.g. hydroxyethylcellulose, hydroxypropylcellulose, polyvinyl alcohol, polyethylene glycol, etc.), stabilizer (e.g. sodium hydrogensulfite, sodium thiosulfate, sodium edetate, sodium citrate, ascorbic acid, dibutylhydroxytoluene, etc.), pH controlling agent (e.g. hydrochloric acid, sodium hydroxide, phosphoric acid, acetic acid, etc.) or the like.

Although the amount of the additive to the above syrup, injection, eye drop and nasal drop depends on the kind and the purpose of the additive to be added, it is sufficient to add the amount of the additive that can achieve the purpose. Usually, an isotonic is added in an amount of about 0.5 to about 5.0 w/v % so that the osmotic pressure reaches about 229 mOsm to about 343 mOsm. Concentrations of buffer, thickner and stabilizer to be added are about 0.01 to about 2.0 w/v %, about 0.01 to about 1.0 w/v % and about 0.001 to about 1.0 w/v %, respectively. A pH controlling agent is appropriately added to adjust the pH usually to about 3 to about 9, preferably about 4 to about 8.

The dose of the compound of the present invention depends on the target diseases, symptom of the disease, subject to be administered, administration route or the like. For example, in the case of oral administration to an adult patient, the dose is about 1 to about 200 mg, preferably about 10 to about 100 mg for a single dose, once to several times a day. In the case of injection to an adult patient, the dose is about 0.1 to about 50 mg, preferably about 1 to about 30 mg, once a day. For topical administration to the eyes, it is preferable to administer eye drops containing usually about 0.001 to about 1.0 w/v %, preferably about 0.01 to about 0.5 w/v %, in an amount of about 20 to about 50 μL per dose, several times a day.

BEST MODE FOR CARRYING OUT THE INVENTION

The present invention will be illustrated below in more detail by way of Reference Examples, Working Examples, Test Examples and Formulation Examples, but it is in no way limited thereto.

In the analytical data of the compounds described in the Examples, melting points were determined on a Yanaco micro melting point apparatus MP-500V without correction. $^1$H-NMR spectra were recorded on a JNM-GSX270 (270 MHz) (JAPAN ELECTRON OPTICS LABORATORY CO., LTD.) and Gemini 2000 (300 MH)(Varian Inc.). The specific optical rotation $[a]_D$ was measured using SEPA-2000 (Horiba, Ltd.). The elementary analysis was measured using CHNSO/2400 (Perkin Elmer, Inc.).

REFERENCE EXAMPLE 1

N-((4-Fluorophenyl)sulfonyl)-L-valyl-L-leucinal (Reference Compound 1)

Step 1: Valine (11.7 g, 100 mmol) was dissolved in 1M aqueous sodium hydroxide (100 mL), and then purified water (150 mL) and tetrahydrofuran (100 mL) were added thereto. The solution was stirred under ice-cooling, and to the solution were dropwise added 1M aqueous sodium hydroxide (100 mL) and a solution of 4-fluorobenzenesulfonyl chloride (17.5 g, 90 mmol) in tetrahydrofuran (100 mL)

simultaneously. The mixed solution was stirred and allowed to react at room temperature for 18 hours. After completion of the reaction, the pH was adjusted to 2 to 3, and the solution was extracted with ethyl acetate. The extract was washed successively with dilute hydrochloric acid and saturated brine, dried over anhydrous magnesium sulfate and concentrated in vacuo to remove ethyl acetate. The residue was washed with a hexane-ethyl acetate mixture (prepared by mixing about 10 to 20 fold amount of hexane with 1 fold amount of ethyl acetate; hereinafter referred to as hexane-ethyl acetate mixture) to give N-((4-fluorophenyl)sulfonyl)-L-valine (15.5 g, 56% yield) as white crystals.

Step 2: N-((4-Fluorophenyl)sulfonyl)-L-valine (15.0 g, 55 mmol) and N-hydroxysuccinimide (7.6 g, 66 mmol) were dissolved in tetrahydrofuran (200 mL). To the solution was gradually added a solution of 1-ethyl-3-(3-dimethylaminopropyl)carbodiimide hydrochloride (12.6 g, 66 mmol) in dichloromethane (200 mL) with stirring under ice-cooling, and the mixture was stirred and allowed to react at room temperature for about 4 hours. After completion of the reaction, the solvent was evaporated off in vacuo and the residue was dissolved in ethyl acetate. The solution was washed successively with dilute hydrochloric acid, saturated aqueous sodium bicarbonate and saturated brine, dried over anhydrous magnesium sulfate and concentrated in vacuo to remove ethyl acetate. The residue was washed with the hexane-ethyl acetate mixture to give N-((4-fluorophenyl)sulfonyl)-L-valine N-hydroxysuccinimide ester (17.6 g, 87% yield) as white crystals.

Step 3: N-((4-Fluorophenyl)sulfonyl)-L-valine N-hydroxysuccinimide ester (2.0 g, 5.4 mmol) was dissolved in dichloromethane (50 mL), and to this solution was added leucinol (0.82 g, 7.0 mmol). The solution was allowed to react while stirring for 2 hours, and washed, after completion of the reaction, successively with dilute hydrochloric acid, saturated aqueous sodium bicarbonate and saturated brine, and dried over anhydrous magnesium sulfate. After removal of the dichloromethane by evaporation in vacuo, the residue was washed with the hexane-ethyl acetate mixture to give N-((4-fluorophenyl)sulfonyl)-L-valyl-L-leucinol (1.9 g, 94% yield) as white crystals.

Step 4: N-((4-Fluorophenyl)sulfonyl)-L-valyl-L-leucinol (1.8 g, 4.8 mmol) was dissolved in dimethyl sulfoxide (20 mL) and dichloromethane (10 mL), and to this solution was added diisopropylethylamine (2.5 g, 19 mmol). To the mixed solution was added a solution of sulfur trioxide-pyridine complex (3.1 g, 19 mmol) in dimethyl sulfoxide (15 mL) while stirring at room temperature. The mixture was further stirred for 40 minutes, and after completion of the reaction, ethyl acetate was added thereto. The reaction mixture was washed successively with dilute hydrochloric acid, saturated aqueous sodium bicarbonate and saturated brine, dried over anhydrous magnesium sulfate and concentrated in vacuo to remove the solvent. The residue was recrystallized from ethyl acetate to give Reference Compound 1 (1.1 g, 60% yield) as white crystals.

M.p. 157° C. $^1$H-NMR (270 MHz, DMSO-$d_6$) δ: 0.74 (d, 3H, J=5.9 Hz), 0.80 (d, 6H, J=6.4 Hz), 0.85 (d, 3H, J=6.8 Hz), 1.14–1.46 (m, 3H), 1.81–1.93 (m, 1H), 3.56–3.62 (dd, 1H, J=6.6, 9.5 Hz), 3.80–3.88 (m, 1H), 7.33–7.42 (m, 2H), 7.79–7.86 (m, 2H), 7.96 (d, 1H, J=9.8 Hz), 8.27 (d, 1H, J=7.3 Hz), 9.14 (s, 1H). Anal. Calcd for $C_{17}H_{25}FN_2O_4S$: C, 54.82; H, 6.77; N, 7.52. Found: C, 54.82; H, 6.76; N, 7.57. $[\alpha]_D^{25}$+8.99° (c=0.20, DMSO).

REFERENCE EXAMPLE 2

(3S)-N-Butyl-3-((2S)-2-(((4-fluorophenyl)sulfonyl)amino)-3-methylbutanoylamino)-2-hydroxy-5-methylhexanamide(Reference Compound 2)

To a solution of Reference Compound 1 (4.0 g, 11 mmol), n-butyl isocyanide (1.0 g, 12 mmol) and pyridine (3.4 g, 43 mmol) in dichloromethane (100 mL) was dropwise added trifluoroacetic acid (2.4 g, 21 mmol) under ice-cooling. The solution was stirred at room temperature for 18 hours, and then concentrated in vacuo. The residue was dissolved in ethyl acetate, and the resultant solution was washed successively with 1M hydrochloric acid, saturated aqueous sodium bicarbonate and saturated brine, dried over anhydrous magnesium sulfate and concentrated in vacuo. The residue was purified by HPLC system (column: YMC Pack ODS-A 250×20 mm I.D.; mobile phase: acetonitrile/water/trifluoroacetic acid=40:60:0.1) to give Reference Compound 2 (1.0 g, 20% yield) as colorless crystals.

M.p. 192.3–194.2° C. $^1$H-NMR (300 MHz, DMSO-$d_6$) δ: 0.69 (d, 3H, J=6.9 Hz), 0.70 (d, 3H, J=5.4 Hz), 0.75 (d, 3H, J=6.0 Hz), 0.79 (d, 3H, J=6.6 Hz), 0.85 (t, 3H, J=7.4 Hz), 0.94 (m, 1H), 1.05–1.09 (m, 2H), 1.18–1.27 (m, 2H), 1.30–1.39 (m, 2H), 1.82 (m, 1H), 2.92–3.07 (m, 2H), 3.63 (dd, 1H, J=9.2, 5.7 Hz), 3.72 (dd, 1H, J=6.0, 2.6 Hz), 3.93 (m, 1H), 5.65 (d, 1H, J=6.0 Hz), 7.31–7.36 (m, 3H), 7.53 (t, 1H, J=5.9 Hz), 7.59 (d, 1H, J=9.2 Hz), 7.80–7.85 (m, 2H).

EXAMPLE 1

(3S)-N-Butyl-3-((2S)-2-(((4-fluorophenyl)sulfonyl)amino)-3-methylbutanoylamino)-5-methyl-2-oxo-hexanamide (Compound 1)

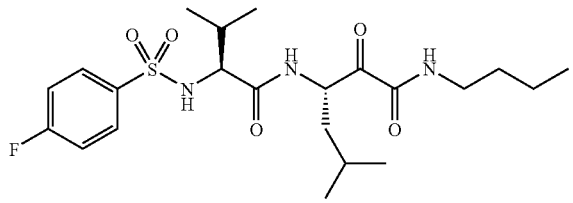

Dess-Martin reagent (Dess-Martin periodinate) (1.3 g, 3.2 mmol) was added to a solution of Reference Compound 2 (1.0 g, 2.1 mmol) in dichloromethane (100 mL). The solution was stirred at room temperature for 18 hours, and 10% aqueous sodium thiosulfate (50 mL) and 10% aqueous sodium bicarbonate (50 mL) were added thereto. After stirring for 10 minutes, the organic layer was separated, washed successively with 1M hydrochloric acid, saturated aqueous sodium bicarbonate and saturated brine, dried over anhydrous magnesium sulfate, and concentrated in vacuo. The residue was crystallized from the hexane-ethyl acetate mixture to give Compound 1 (0.80 g, 80% yield) as colorless crystals.

M.p. 107.6–109.9° C. $^1$H-NMR (300 MHz, DMSO-$d_6$) δ: 0.73 (d, 3H, J=5.7 Hz), 0.79–0.88 (m, 12H), 1.15–1.45 (m, 7H), 1.82 (m, 1H), 3.04–3.11 (m, 2H), 3.59 (m, 2H), 4.75 (m, 1H), 7.33–7.39 (m, 2H), 7.78–7.83 (m, 2H), 7.88 (d, 1H, J=9.3 Hz), 8.15 (d, 1H, J=6.3 Hz), 8.65 (t, 1H, J=5.9 Hz). Anal. Calcd for $C_{22}H_{34}N_3O_5SF$: C, 56.03; H, 7.27; N, 8.91. Found: C, 55.99; H, 7.00; N, 8.91.

TEST EXAMPLE 1

(1) Measurement of Inhibitory Activity Against μ-Calpain and m-Calpain

The inhibitory activity against μ-calpain and m-calpain was assayed according to the method described in Anal. Biochem. 1993, vol. 208, p. 387–392. That is, to 2.5 μL of a dimethyl sulfoxide (DMSO) solution containing a varying concentration of the test compound in a 96-well plate was added 200 μL of a reaction solution containing 0.5 mg/mL casein, 50 mM Tris-HCl buffer (pH 7.4), 20 mM dithiothreitol and 1.0 nmol μ-calpain (derived from human red blood cells; available from Cosmo Bio Co. Ltd.) or m-calpain (derived from porcine kidney; available from Cosmo Bio Co. Ltd.). After 20 mM aqueous calcium chloride (50 μL) was added thereto, the mixture was incubated at 30° C. for 60 minutes. Then, 100 μL of the reaction solution was transferred to another 96-well plate, and purified water (50 μL) and 50% aqueous solution (100 μL) of Protein Assay Dye Reagent (available from Bio-Rad Laboratories, Inc.; catalogue No. 500–600) were added thereto. The reaction mixture was allowed to stand at room temperature for 15 minutes, and its absorbance was measured at 595 nm.

The absorbance of a reaction mixture prepared in the same manner as mentioned above, except that a DMSO solution contained no test compound, was used as a control value, and that of a reaction mixture prepared in the same manner as mentioned above, except that 1 mM aqueous EDTA solution (50 μL) was used in place of 20 mM aqueous calcium chloride, was used as a blank value, and accordingly the concentration required for 50% inhibition ($IC_{50}$) was determined.

Inhibition rate (%)={1−(measured value minus blank value)/(control value minus blank value)}×100

RESULTS OF TEST EXAMPLE 1

The calpain inhibitory activities are shown in Table 1.

TABLE 1

Inhibitory activities of the compound of the invention against μ-calpain and m-calpain

| Test Compounds (Compound No.) | 50% Inhibition Concentration of Enzyme Activity [$IC_{50}$ (μM)] | |
|---|---|---|
| | μ-calpain | m-calpain |
| 1 | 0.021 | 0.021 |

As a result of the above test, the compound of the present invention was proven to have excellent inhibitory activity against calpain.

TEST EXAMPLE 2

Permeability Test with Caco-2 Cells $0.5 \times 10^6/cm^2$ of Caco-2 cells (ATCC Catalog No. HTB-37, Manassas, Va., USA) were seeded into Transwell (polycarbonate filter: pore diameter 0.4 μm; culture area 0.33 $cm^2$; available from Costar Co.), and incubated in Dulbecco's modified Eagle's minimum essential medium (DMEM; available from Fisher Scientific International Inc.) for 21 to 30 days under the conditions of 37° C., 5% $CO_2$ and 95% relative humidity, whereby a monolayer cell was prepared. The confluence of such a monolayer cell was evaluated by measuring trans epithelial electronic resistance (TEER). A Hanks' Balanced Salt Solution (referred to as HBSS; available from Fisher Scientific International Inc.) was added to Compound 1 at apical membrane side to a concentration of 10 μM, and HBSS was added to basolateral membrane side. Concentration of Compound 1 at the basolateral membrane side after 30 minutes and 60 minutes, and concentration of Compound 1 at the apical membrane side after 60 minutes were quantified by high performance liquid chromatography. Based on the quantification results, apparent permeation coefficient ($P_{app}$) was calculated according to the formula:

$$P_{app}=(\delta Q/\delta t) \times (1/60 A C_0).$$

$P_{app}$: apparent permeation coefficient (cm/sec)
$\delta Q/\delta t$: permeation velocity (pmol/min)
A: area of monolayer cell=0.33 $cm^2$
$C_0$: initial concentration at apical membrane side (pmol/mL)

RESULTS OF TEST EXAMPLE 2

The apparent permeation coefficient ($P_{app}$) of Compound 1 was $1.7 \times 10^{-5}$ (cm/sec).

| Formulation Example 1: Tablet | |
|---|---|
| Compound 1 | 5 g |
| Starch | 12 g |
| Lactose | 27.2 g |
| Magnesium stearate | 0.4 g |

Compound 1, lactose and starch were blended well, and formulated into granules for tableting according to the wet granule tableting method. After addition of magnesium stearate, the granules were compressed to make 400 tablets. The tablets were, if required, coated with an enteric coating agent (methacrylic acid copolymer).

| Formulation Example 2: Eye drops | |
|---|---|
| Compound 1 | 100 mg |
| Boric acid | 700 mg |
| Borax | q.s. |
| Sodium chloride | 500 mg |
| Sodium edetate | 0.05 mg |
| Benzalkonium chloride | 0.0005 mg |
| Sterile purified water to make a total volume of 100 ml | |

The above components were mixed under sterile conditions according to the conventional method to prepare eye drops.

| Formulation Example 3: Injection | |
|---|---|
| Compound 1 | 100 mg |
| Sodium chloride | 900 mg |
| 1N Sodium hydroxide | q.s. |
| Distilled water for injection to make total volume | 100 mL |

The above components were mixed under sterile conditions according to the conventional method to prepare an injection preparation.

INDUSTRIAL APPLICABILITY

Since the compounds of the formula (I) of the present invention have excellent calpain inhibitory activity, they are useful as a prophylactic and therapeutic agent for various diseases related to calpain such as ischemic disease, immunologic disease, Alzheimer's disease, osteoporosis, diseases caused by brain tissue damage, cataract, glaucoma, retinal disease, retinochoroidal disease, posterior eyeball complications due to photocoagulation or a disease involving neovascularization.

Although certain specific embodiments of the present invention are explained in detail above, since it is possible for those skilled in the art to make various modifications or changes in the specific embodiments without substantially departing from the novel teachings and advantages of the present invention, and thus such modifications or changes are all encompassed in the spirit and scope of the present invention defined by claims mentioned below.

The present invention is based on Japanese patent application No. 2002-212288, and all the content of which is hereby incorporated by reference.

The invention claimed is:

1. A compound represented by the formula (I)

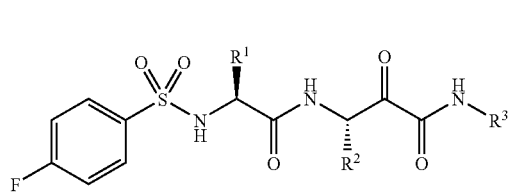

wherein $R^1$, $R^2$ and $R^3$ each represents a lower alkyl group.

2. The compound as claimed in claim 1, wherein $R^1$, $R^2$ and $R^3$ each represents an alkyl group having 3 or 4 carbon atoms.

3. (3S)-N-butyl-3-((2S)-2-(((4-fluorophenyl)sulfonyl)amino)-3-methylbutanoylamino)-5-methyl-2-oxohexanamide.

4. A pharmaceutical composition comprising a compound represented by the formula (I)

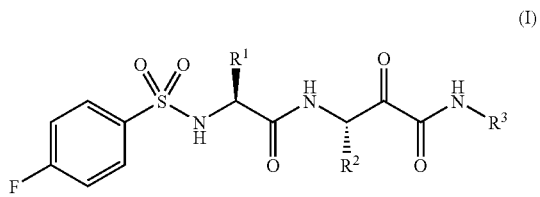

wherein $R^1$, $R^2$ and $R^3$ each represents a lower alkyl group, and a pharmaceutically acceptable carrier.

5. The pharmaceutical composition as claimed in claim 4, which is a calpain inhibitor.

6. A method for the treatment of a disease related to calpain, which comprises administering an effective amount of a compound represented by the formula (I)

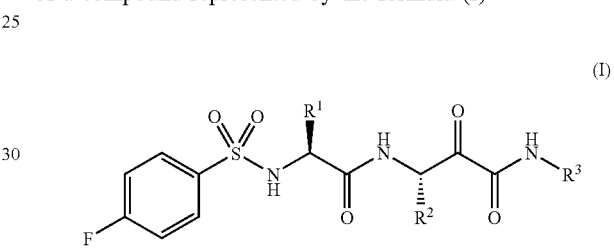

wherein $R^1$, $R^2$ and $R^3$ each represents a lower alkyl group, to a mammal in need of treatment.

* * * * *